United States Patent [19]

Matsuno et al.

[11] Patent Number: 4,613,456
[45] Date of Patent: Sep. 23, 1986

[54] TRICYCLO[2.2.1.0$^{2,6}$]HEPTANE DERIVATIVES, PROCESS FOR PREPARING SAME, AND PERFUME COMPOSITIONS CONTAINING SAME

[75] Inventors: Mitsuo Matsuno, Kawasaki; Teraki Yamanashi, Yokohama; Hitoshi Yuasa, Yokohama; Hirosuke Imai, Yokohama, all of Japan

[73] Assignee: Nippon Oil Co. Ltd., Japan

[21] Appl. No.: 735,341

[22] Filed: May 17, 1985

[30] Foreign Application Priority Data

May 18, 1984 [JP] Japan .................................. 59-98634

[51] Int. Cl.$^4$ ........................... C11B 9/00; A61K 7/46
[52] U.S. Cl. .................................. 252/522 R; 568/821
[58] Field of Search ....................... 252/522 R, 522 A; 568/821

[56] References Cited

U.S. PATENT DOCUMENTS 3,944,621  3/1976  Mookherjee et al. .......... 252/522 R
3,977,418  8/1976  Francisco et al. .................. 131/276
4,014,823  3/1977  Mookherjee et al. .......... 252/522 R
4,208,297  6/1980  Light et al. ..................... 252/174.11
4,442,025  4/1984  Boelen et al. ................... 252/522 R Primary Examiner—Werren B. Lone
Attorney, Agent, or Firm—McGlew and Tuttle

[57] ABSTRACT

This invention discloses a tricyclo[2.2.1.0$^{2,6}$]heptane derivative of the general formula

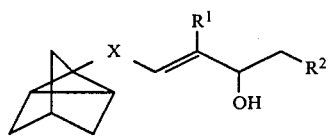

where X represents —CH$_2$CH$_2$— or

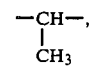

and R$^1$ and R$^2$ independently represent hydrogen or methyl, a process for preparing the same, and perfume compositions containing the same.

7 Claims, 2 Drawing Figures

TRICYCLO[2.2.1.0²,⁶]HEPTANE DERIVATIVES, PROCESS FOR PREPARING SAME, AND PERFUME COMPOSITIONS CONTAINING SAME

BACKGROUND OF THE INVENTION

1. Field of the Invention

This invention relates to novel tricyclo[2.2.1.0$^{2,6}$]heptane derivatives, a process for preparing the same, and perfume compositions containing the same.

2. Description of the Prior Art

It has conventionally been known that some compounds having the tricyclo[2.2.1.0$^{2,6}$]heptyl group are useful as perfumes. Typical of such compounds is α-santalol which is one of the principal components of sandalwood oil. Moreover, it is disclosed in U.S. Pat. Nos. 3,944,621, 3,977,418 and 4,014,823, Japanese Patent Laid-Open No. 140733/'79 and the like that compounds having a tricyclo[2.2.1.0$^{2,6}$]heptane structure can be utilized as perfumes or deodorants.

However, in most of the compounds disclosed in these references, the substituent group governing their functionality is attached to the 3-position of the tricyclo[2.2.1.0$^{2,6}$]heptane ring. Although some compounds have a substituent group introduced into the 1-position of the ring, such a substituent group is no more than a simple alkyl group such as methyl or ethyl. Such a simple substituent group attached to the 1-position of the ring has a slight influence on the functionality of the compound, but never affects the essential nature of its functionality.

The present inventors have found that certain compounds having a functionality-governing substituent group introduced into the 1-position of the tricyclo[2.2.1.0$^{2,6}$]heptane ring give out a sandalwood-like fragrance having a bouquet odor as the top note and are very useful as materials for use in perfume preparations. The present invention has been completed on the basis of this discovery.

SUMMARY OF THE INVENTION

It is an object of the present invention to provide a novel tricyclo[2.2.1.0$^{2,6}$]heptane derivative having a functionality-governing substituent group introduced into the 1-position of the tricyclo[2.2.1.0$^{2,6}$]heptane ring.

It is another object of the present invention to provide a process for preparing such a novel tricyclo[2.2.1.0$^{2,6}$]heptane derivative.

It is still another object of the present invention to provide a perfume composition containing such a novel tricyclo[2.2.1.0$^{2,6}$]heptane derivative.

According to a first aspect of the present invention, there is provided a tricyclo[2.2.1.0$^{2,6}$]heptane derivative of the general formula

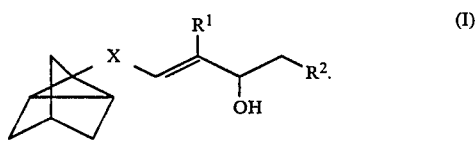
(I)

where X represents —CH$_2$CH$_2$— or

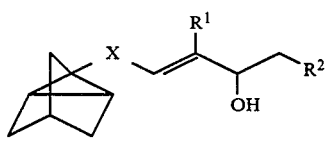

and R$^1$ and R$^2$ independently represent hydrogen or methyl. In this specification, X, R$^1$ and R$^2$ will hereafter have the same meanings as described above.

According to a second aspect of the present invention, there is provided a process for preparing a tricyclo[2.2.1.0$^{2,6}$]heptane derivative of the general formula

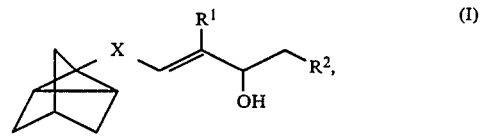
(I)

which comprises (a) reacting an aldehyde compound of the general formula

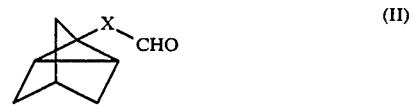
(II)

with a dialkyl ketone of the general formula

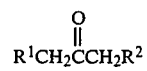

$$R^1CH_2CCH_2R^2$$

in the presence of an aldol condensation catalyst to obtain an α,β-unsaturated ketone of the general formula

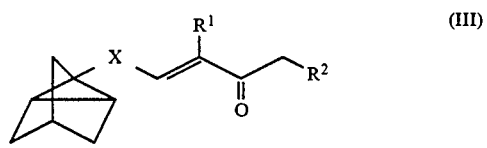
(III)

and then (b) reducing the resulting α,β-unsaturated ketone.

According to a third aspect of the present invention, there is provided a perfume composition containing a tricyclo[2.2.1.0$^{2,6}$]heptane derivative of the general formula

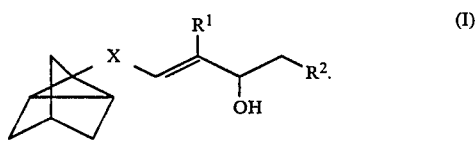
(I)

DETAILED DESCRIPTION OF THE PREFERRED EMBODIMENTS

Figure 1:
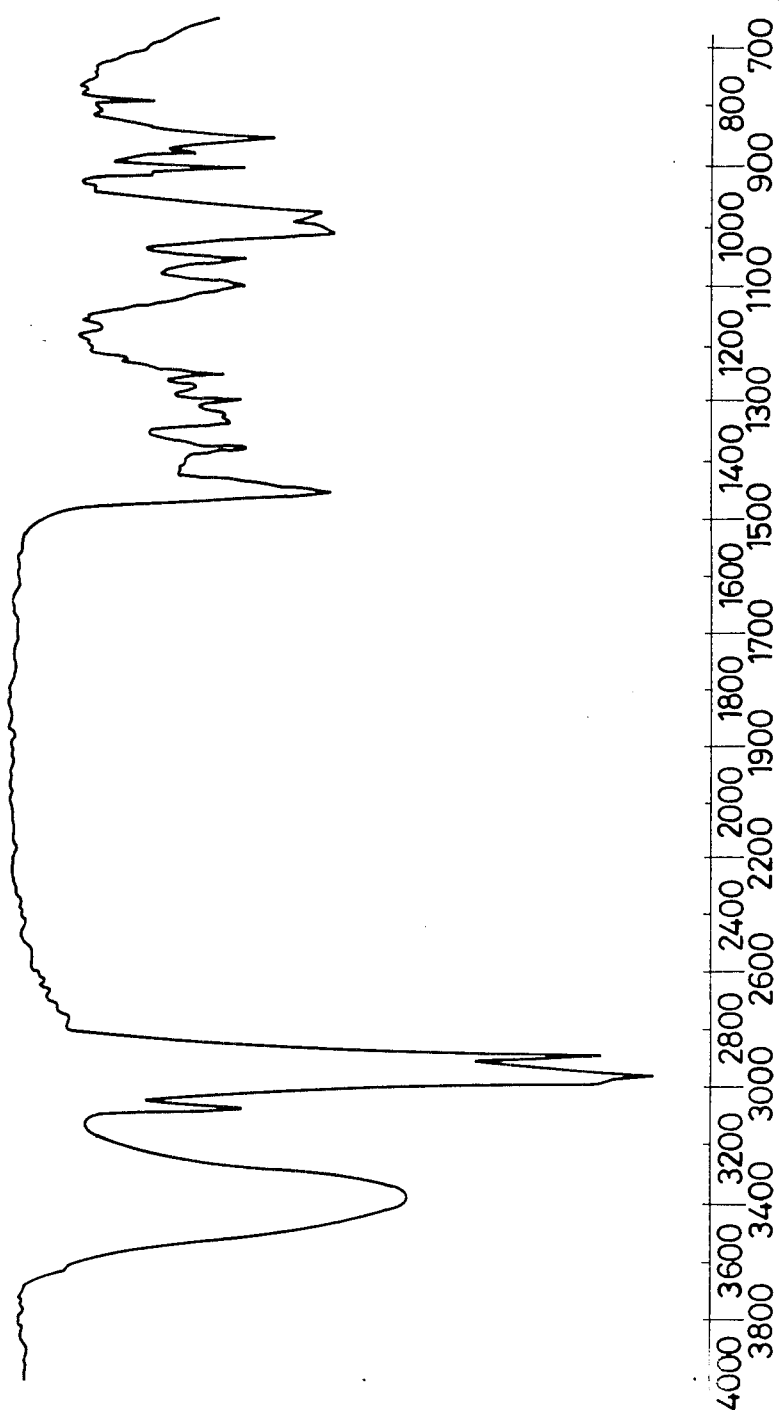
FIG. 1 is a diagram showing the infrared spectrum of 4-methyl-7-(tricyclo[2.2.1.0$^{2,6}$]hept-1'-yl)-hept-4-en-3-ol, the values given therein being expressed in cm$^{-1}$.
Figure 2:
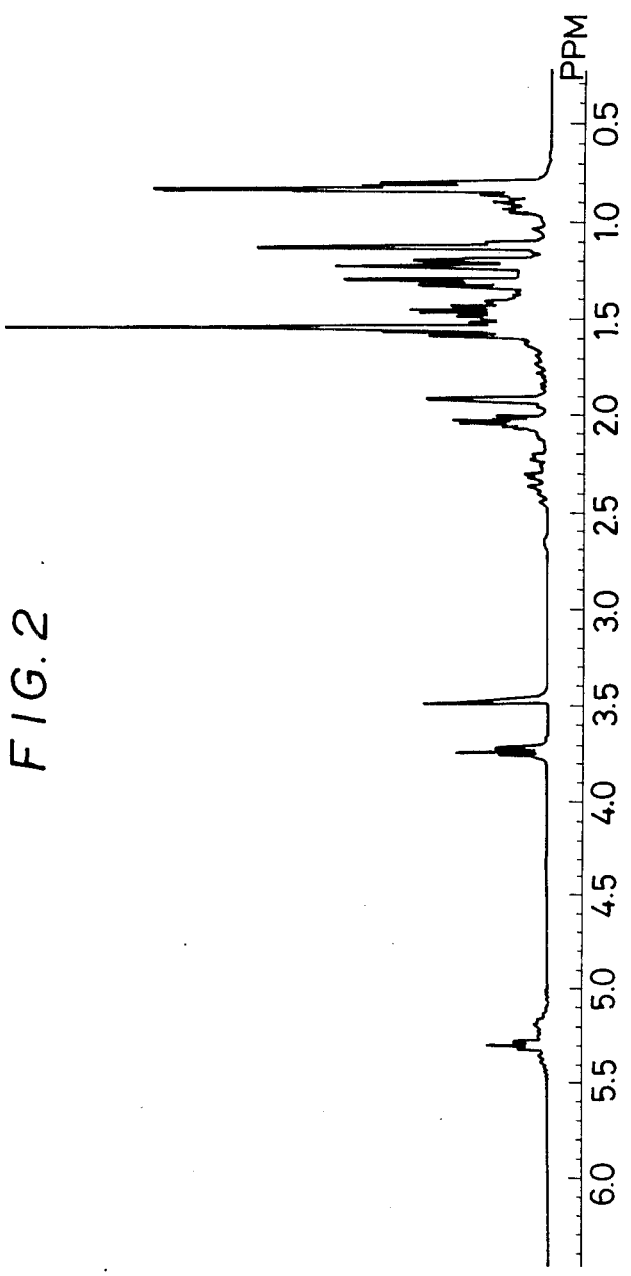
FIG. 2 is a diagram showing the NMR spectrum of the aforesaid compound, the values given therein being δ values obtained by using TMS as a reference compound.

The tricyclo[2.2.1.0$^{2,6}$]heptane derivatives (I) of the present invention are novel compounds which have never been known in the prior art. The aldehyde compound (II) used in the synthesis of these derivatives can be prepared by introducing a formyl group into 1-ethenyltricyclo[2.2.1.0$^{2,6}$]heptane (IV), as shown in the equation given below. This can be done by the utilization of such techniques as hydroformylation and the like. Usually, the aldehyde compound (II) thus obtained is a mixture of two structural isomers as shown in the following equation.

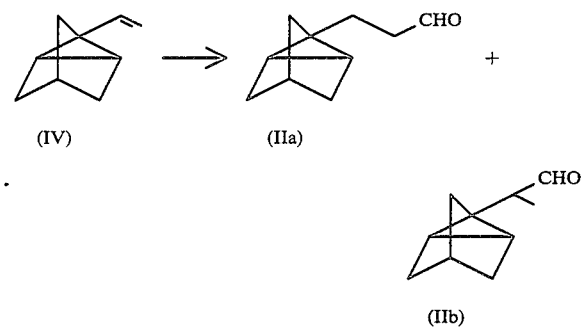

These two isomers can be separated by such techniques as precise fractionation and the like. When each of the separated isomers (IIa) and (IIb) is used in the process of the present invention, both of the resulting two isomeric tricyclo[2.2.1.0$^{2,6}$]heptane derivatives (I) emit a sandalwood-like fragrance having a bouquet note. However, their odors are slightly different from each other. Nevertheless, when the aldehyde compound is used in the synthesis of perfumes, it is preferable to use the mixture of isomers directly without separating them. This is because the mixture of two isomeric tricyclo[2.2.1.0$^{2,6}$]heptane derivatives (I) obtained by using the mixture of aldehyde compounds (IIa) and (IIb) as a reactant exhibits a depth of fragrance which cannot be obtained with each of the two derivatives.

The dialkyl ketone used in the process of the present invention is at least one compound selected from acetone, 2-butanone and 3-pentanone. Among these compounds, 3-pentanone is especially preferred.

As the catalyst for the aldol condensation in the process of the present invention, there may be used acid substances and basic substances. Useful acid substances include inorganic acids such as hydrochloric acid, sulfuric acid, phosphoric acid, etc.; organic acids such as benzenesulfonic acid, toluenesulfonic acid, naphthalenesulfonic acid, trifluoroacetic acid, trichloroacetic acid, etc.; and cation exchange resins. Useful basic substances include metal hydroxides such as lithium hydroxide, sodium hydroxide, potassium hydroxide, cesium hydroxide, rubidium hydroxide, barium hydroxide, etc.; metal alkoxides such as lithium methoxide, sodium methoxide, potassium methoxide, lithium ethoxide, sodium ethoxide, potassium ethoxide, potassium t-butoxide, magnesium ethoxide, aluminum isopropoxide, etc.; metal carbonates such as sodium carbonate, potassium carbonate, cesium carbonate, etc.; and quaternary ammonium hydroxides such as tetramethylammonium hydroxide, benzyltrimethylammonium hydroxide, etc. Other basic catalysts include lithium hydride, sodium hydride, potassium hydride, lithium amide, sodium amide, potassium amide, lithium diisopropylamide, tertiary amines, active methylene alkali metal compounds, weakly acidic organic or inorganic alkali metal salts, alkali metal oxides, alkaline earth metal oxides and the like. Among these catalysts, alkali metal hydroxides, alkali metal alkoxides, quaternary ammonium hydroxides and alkali metal amides are especially preferred.

No particular limitation is placed on the reaction conditions under which the aldol condensation is carried out. However, the reaction temperature generally ranges from 0° to 200° C. and preferably from 30° to 100° C. The reaction pressure may be atmospheric, superatmospheric or subatmospheric.

Although the aldol condensation may be carried out in the absence of solvent, it is preferable to use a solvent for the purpose of bringing the reactants into close contact with the catalyst and suppressing side reactions such as the Cannizzaro reaction and the reaction of the resulting $\alpha,\beta$-unsaturated ketone with unreacted aldehyde. As the solvent, there may be used dialkyl ketones added in excess of their stoichiometric amount, alcohols, water, saturated hydrocarbons, ethers, halogenated hydrocarbons and the like, as well as mixtures of the foregoing. In the case of a heterogeneous reaction system in which the reactants do not mix homogeneously with the catalyst, a quaternary ammonium salt such as benzyltrimethylammonium bromide may be used as a phase transfer catalyst.

In the aldol condensation step, it sometimes happens that the aldol formed by the condensation is recovered as such. However, the process of the present invention requires no dehydration step because the aldol so formed easily dehydrates to produce an unsaturated ketone. Nevertheless, especially when the condensation is carried out at low temperatures, an unsaturated ketone can be easily obtained by heating the reaction mixture, with or without a dehydrating agent, subsequently to the aldol condensation step.

In order to prevent self-condensation of the aldehyde compound during the aldol condensation, it is preferable to increase the molar ratio of the dialkyl ketone to the aldehyde compound. However, if the molar ratio is excessively high, not only it is poor economy, but also the concentration of the aldehyde compound in the reaction system is lowered to decelerate the reaction and result in a reduction in yield. Accordingly, the molar ratio of the dialkyl ketone to the aldehyde compound should be in the range of 1 to 20 and preferably in the range of 3 to 10.

Then, the carbonyl group of the unsaturated ketone is reduced to obtain the desired tricyclo[2.2.1.0$^{2,6}$]heptane derivative (I). In this reduction step, it is necessary to reduce the carbonyl group selectively while leaving the carbon-to-carbon double bond unreduced and thereby produce an unsaturated alcohol. Thus, the reducing agent used in this step is preferably selected from metal hydrides, combinations of an alcohol and an aluminum alkoxide, combinations of an alcohol and an alkali metal or alkaline earth metal alkoxide, and the like. Moreover, this reduction step may also be carried out by catalytic reduction using a suitable catalyst system or by electrolytic reduction.

Useful metal hydrides include, for example, lithium brohydride, sodium borohydride, lithium aluminum hydride and sodium aluminum hydride, as well as the compounds obtained by replacing one to three hydrogen atoms of these metal hydrides with alkoxyl groups (such as methoxyl, ethoxyl, etc.) or cyano groups. In addition, lithium hydride, sodium hydride, potassium hydride and the like are also useful. In the reduction system using an alcohol and an aluminum alkoxide (i.e., the Meerwein-Ponndorf reduction), it is preferable to use isopropyl alcohol as the alcohol and aluminum isopropoxide as the aluminum alkoxide. Alternatively, in this reduction system, an alkali metal or alkaline earth metal alkoxide may be used in place of the aluminum alkoxide.

In the reduction step, there may be used one or more solvents selected from the alcohols such as methanol, ethanol, isopropanol, etc.; ethers such as dioxane, diethyl ether, tetrahydrofuran, etc.; saturated aliphatic hydrocarbons; aromatic or aliphatic alkyl esters; and the like.

The reduction step is usually carried out at a temperature in the range of 0° to 150° C.

After completion of the reduction, the solvent is distilled off from the reaction mixture and the resulting residue is post-treated according to conventional procedure. The resulting organic phase is isolated and purified to obtain the desired tricyclo[2.2.1.0$^{2,6}$]heptane derivative (I).

Typical examples of the tricyclo[2.2.1.0$^{2,6}$]heptane derivative (I) include 4-methyl-7-(tricyclo[2.2.1.0$^{2,6}$-]hept-1'-yl)hept-4-en-3-ol, 4-methyl-6-(tricyclo[2.2.1.0$^{2,6}$]hept-1'-yl)hept-4-en-3-ol, 7-(tricyclo[2.2.1.0$^{2,6}$]hept-1'-yl)hept-4-en-3-ol, 6-(tricyclo[2.2.1.0$^{2,6}$]hept-1'-yl)hept-4-en-3-ol, 3-methyl-6-(tricyclo[2.2.1.0$^{2,6}$]hept-1'-yl)hex-3-en-2-ol, 3-methyl-5-(tricyclo-2.2.1.0$^{2,6}$]hept-1'-yl)-hex-3-en-2-ol, 6-(tricyclo[2.2.1.0$^{2,6}$]hept-1'-yl)hex-3-en-2-ol and 5-(tricyclo[2.2.1.0$^{2,6}$]hept-1'-yl)hex-3-en-2ol.

Since the tricyclo[2.2.1.0$^{2,6}$]heptane derivatives (I) of the present invention basically has a woody fragrance, they may preferably be used as components of perfume compositions having a woody note. Moreover, if they are blended in perfume compositions having such odors as floral note, bouquet note, modern note, green note, cypre note, leather note, oriental note, citrus note, fougere note and the like, theperfume compositions will emit a unique fragrance. Thus, the aforesaid tricyclo[2.2.1.0$^{2,6}$]heptane derivatives can be used in a wide variety of perfume compositions. Perfume compositions containing the aforesaid tricyclo[2.2.1.0$^{2,6}$]heptane derivatives have wide applications including perfume preparations, cosmetics, soaps, detergents, shampoos, hair rinses and other articles for daily use.

The present invention is more fully explained with reference to a reference example and several examples.

REFERENCE EXAMPLE

Synthesis of 3-(tricyclo[2.2.1.0$^{2,6}$]hept-1'-yl)propanal and 2-(tricyclo[2.2.1.0$^{2,6}$]hept-1'-yl)propanal Into a 2-liter stainless steel autoclave fitted with a stirrer and a thermocouple were charged 720 g of 1-ethenyltricyclo[2.2.1.0$^{2,6}$]heptane (IV), 1.1 g of the catalyst RhH(CO) (PPh$_3$)$_3$ and 300 ml of toluene. After the autoclave was hermetically sealed, it was flushed twice with a synthesis gas (H$_2$:CO=1:1) to substitute the air present therein. Then, the reaction mixture within the autoclave was heated with stirring until it reached 60° C. Under these conditions, a synthesis gas (H$_2$:CO=1:1) was introduced under pressure into the autoclave to keep its internal pressure at 100 kg/cm$^2$. After 30 hours, the autoclave was cooled to room temperature and then purged off the unreacted gas. Thereafter, the reaction mixture was withdrawn. This reaction mixture was roughly distilled to obtain 628 g of a fraction boiling at 45° C./2 mmHg to 69° C./2 mmHg. Using a spinning band fractionating column, this fraction was vacuum distilled to obtain 110.6 g of 2-(tricyclo[2.2.1.0$^{2,6}$]hept-1'-yl)propanal (IIb), B.P. 50° C./2 mmHg, and 374.6 g of 3-(tricyclo[2.2.1.0$^{2,6}$-]hept-1'-yl)propanal (IIa), B.P. 62° C./2 mmHg.

EXAMPLE 1

Synthesis of 4-methyl-7-(tricyclo[2.2.1.0$^{2,6}$]hept-1'-yl)hept-4-en-3-ol

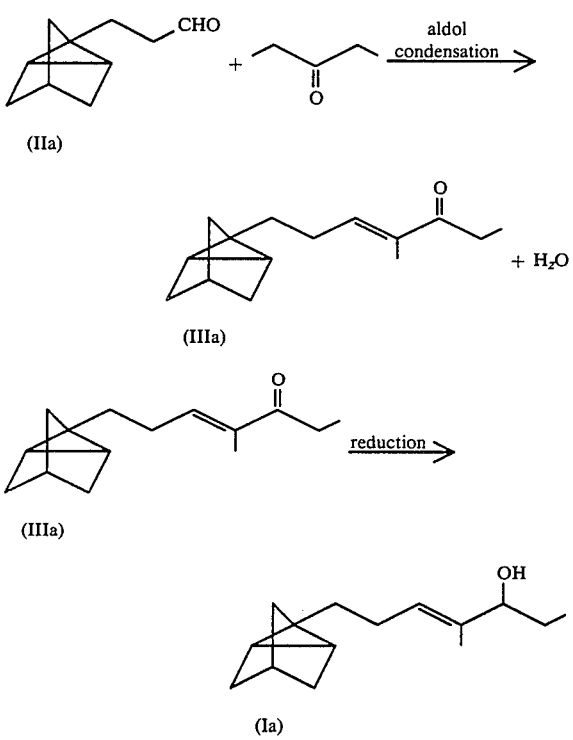

156.8 g (1.82 moles) of 3-pentanone was dissolved in 200 ml of methanol. To the resulting solution were added 10 g of a 40% aqueous solution of sodium hydroxide and then 90.9 g (0.605 mole) of 3-(tricyclo[2.2.1.0$^{2,6}$]hept-1'-yl)propanal (IIa). The resulting mixture was heated at the boiling temperature of methanol for 2 hours to effect aldol condensation. The reaction mixture was post-treated according to conventional procedure and then vacuum distilled to obtain the α,β-unsaturated ketone (IIIa) in an 85% yield. This product was identified as the α,β-unsaturated ketone (IIIa) on the basis of its infrared spectrum and NMR spectrum.

Then, 18.9 g of an aqueous sodium hydroxide solution containing 12% of sodium borohydride (manufactured by Nisso-Bentron Co., Ltd.) and 120 ml of methanol were placed in a flask. While this mixture was being stirred, 34.9 g (0.160 mole) of the above α,β-unsaturated ketone was added dropwise thereto. After completion of the addition, the reaction was continued at 60° C. for an additional two hours. After completion of the reaction, the methanol used as the solvent was distilled off from the reaction mixture. The resulting residue was washed with water until it became neutral, dried over anhydrous sodium sulfate and then vacuum distilled to obtain 33.3 g of the desired compound, or 4-methyl-7-(tricyclo[2.2.1.0$^{2,6}$]hept-1'-yl)hept-4-en-3-ol (Ia), in a 96.4% yield. This product was a colorless, oily substance boiling at 118°–124° C./1.0 mmHg and emitted a sandalwood-like fragrance having a gorgeous bouquet odor as the top note. The results of its analyses are given in the following.

Mass spectrum: M$^{30}$=220 m/e.

Infrared spectrum: The OH stretching vibration is observed at ~3400 cm$^{-1}$, and absorption bands characteristic of tricyclo[2.2.1.0$^{2,6}$]heptane compounds are observed at 790 cm$^{-1}$ and 855 cm$^{-1}$. The absorption band (at 1670 cm$^{-1}$) arising from the carbonyl group present in the α,β-unsaturated ketone (IIIa) has disappeared as a result of the reduction.

NMR spectrum: δ 0.8 (Triplet, 3H); δ 0.9–1.0 (Multiplet, 2H); δ 1.1–1.3 (Multiplet, 6H); δ 1.4–1.5 (multiplet, 2H); δ 1.5 (Singlet, 3H); δ 1.9 (Singlet, 1H); δ 2.1 (Multiplet, 2H); δ 2.2–2.5 (Multiplet, 2H); δ 3.5 (Singlet, 1H); δ3.7 (Triplet, 1H); δ5.3 (Triplet, 1H).

Elementary analysis: Calculated for C$_{15}$H$_{24}$O C, 81.76%, H, 10.98%. Found C, 81.58%; H, 10.82%.

EXAMPLE 2

Synthesis of 4-methyl-6-(tricyclo[2.2.1.0$^{2,6}$]hept-1'-yl)hept-4-en-3-ol

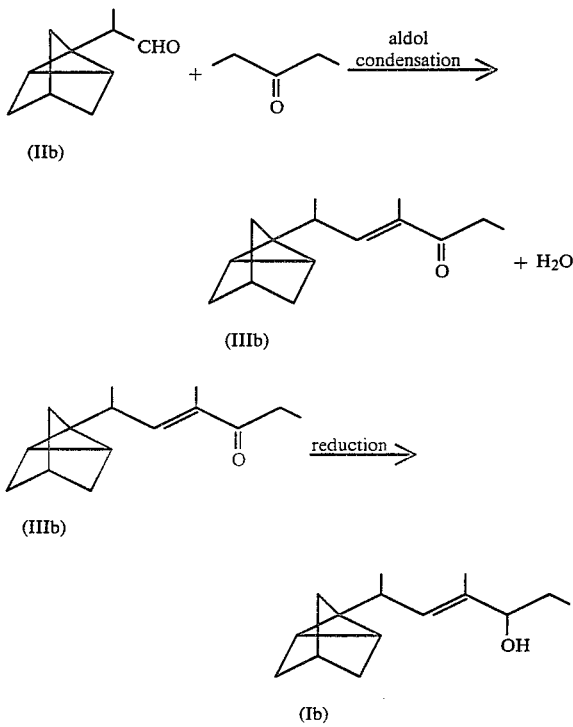

Aldol condensation was carried out in the same manner as described in Example 1, except that 2-(tricyclo[2.2.1.0$^{2,6}$]hept-1'-yl)propanal (IIb) was used in place of 3-(tricyclo[2.2.1.0$^{2,6}$]hept-1'-yl)propanal. Thus, there was obtained the α,β-unsaturated ketone (IIIb) in an 89% yield.

In the same manner as described in Example 1, 31.5 g (0.144 mole) of the above α,β-unsaturated ketone (IIIb) was reduced in the presence of 17.1 g of an aqueous sodium hydroxide solution containing 0.054 mole of sodium borohydride and 120 ml of methanol. Thereafter, the reaction mixture was post-treated and then vacuum distilled to obtain 29.5 g of 4-methyl-7-(tricyclo[2.2.1.0$^{2,6}$]hept-1'-yl)hept-4-en-3-ol (Ib) in a 95% yield. This product also was an oily substance emitting a sandalwood-like pleasant fragrance with a floral note. The results of its analyses are given in the following.

Mass spectrum: M$^{+}$=220 m/e.

Infrared spectrum: The OH stretching vibration is observed at ~3400 cm$^{-1}$, and absorption bands characteristic of tricyclo[2.2.1.0$^{2,6}$]heptane compounds are observed at 790 cm$^{-1}$ and 855 cm$^{-1}$.

NMR spectrum: δ 0.8 (Triplet, 3H); δ 0.9 (Multiplet, 4H); δ 1.1–1.3 (Multiplet, 6H); δ 1.4–1.5 (Multiplet, 3H); δ 1.6 (Singlet, 3H); δ 1.9 (Singlet, 1H); δ 2.6 (Multiplet, 1H); δ 3.1 (Singlet, 1H); δ 3.8 (Triplet, 1H); δ 5.2 (Doublet, 1H).

Elementary analysis: Calculated for C$_{15}$H$_{24}$O C, 81.76%; H, 10.98%. Found C, 81.37%; H, 10.56%.

EXAMPLE 3

Synthesis of 4-methyl-6-(tricyclo[2.2.1.0$^{2,6}$]hept-1'-yl)hept-4-en-3-ol and 4-methyl-7-(tricyclo[2.2.1.0$^{2,6}$]hept-1'-yl)hept-4-en-3-ol The procedure of Example 1 was repeated except that the mixture of 2-(tricyclo[2.2.1.0$^{2,6}$]hept-1'-yl)propanal (IIb) and 3-(tricyclo[2.2.1.0$^{2,6}$]hept-1'-yl)propanal (IIa) obtained by hydroformylating 1-ethenyltricyclo[2.2.1.0$^{2,6}$]heptane (IV) in the same manner as described in Reference Example was directly used without subjecting it to fractionation. Thus, there was obtained a mixture of the α,β-unsaturated ketones (IIIa) and (IIIb) in a 90% yield.

37.4 g (0.171 mole) of the above unsaturated ketone mixture was dissolved in 500 ml of isopropyl alcohol. To the resulting solution was added 3.4 g of aluminum isopropoxide. The resulting mixture was heated under reflux, during which the formed acetone was distilled off. After 20 hours, the reaction mixture freed of acetone was distilled under reduced pressure to remove isopropyl ether. After the addition of dilute sulfuric acid to the residue, the resulting mixture was extracted with n-hexane. The isolated organic phase was washed with water, dried and then vacuum distilled to obtain the desired mixture of 4-methyl-7-(tricyclo[2.2.1.0$^{2,6}$]hept-1'-yl)hept-4-en-3-ol (Ia) and 4-methyl-6-(tricyclo[2.2.1.0$^{2,6}$]hept-1'-yl)hept-4-en-3-ol (Ib) in a 90% yield.

The boiling point, infrared spectrum and NMR spectrum of this product were similar to those of a mixture of the compounds obtained in Examples 1 and 2.

EXAMPLE 4

Synthesis of 3-methyl-6-(tricyclo[2.2.1.0$^{2,6}$]hept-1'-yl)hex-3-en-2-ol

Aldol condensation was carried out in the same manner as described in Example 1, except that 144.2 g (2.0 moles) of methyl ethyl ketone was used in place of diethyl ketone. Thus, there was obtained the corresponding α,β-unsaturated ketone, or 3-methyl-6-tricyclo[2.2.1.0$^{2,6}$]hept-1'-yl)hex-4-en-3-one, in an 80% yield. Then, this α,β-unsaturated ketone was reduced in the same manner as described in Example 1 to obtain the desired compound, or 3-methyl-6-(tricyclo[2.2.1.0$^{2,6}$]hept-1'-yl)hex-3-en-2-ol, in a 96% yield. This product was a colorless, oily substance boiling at 109°–114°

C./1.0 mmHg and having a fougere note. The results of its analyses are given in the following.

Mass spectrum: M+ = 220 m/e.

Infrared spectrum: The OH stretching vibration is observed at ~3400 cm$^{-1}$, and absorption bands characteristic of tricyclo[2.2.1.0$^{2,6}$]heptane compounds are observed at 790 cm$^{-1}$ and 855 cm$^{-1}$.

NMR spectrum: δ 0.9–1.0 (Multiplet, 2H); δ 1.1–1.3 (Multiplet, 9H); δ 1.5 (Singlet, 3H); δ 1.9 (Singlet, 1H); δ 2.1 (Multiplet, 2H); δ2.2–2.5 (Multiplet, 2H); δ 3.7 (Singlet, 1H); δ 3.9 (Triplet, 1H); δ 5.3 (Triplet, 1H).

Elementary analysis: Calculated for $C_{15}H_{24}O$ C, 81.50%, H, 10.75%. Found C, 81.63%; H, 10.59%.

EXAMPLE 5

Using the tricyclo[2.2.1.0$^{2,6}$-]heptane derivative obtained in Example 1, a perfume composition for use in eaux de Cologne was prepared according to the following formulation.

| Ingredient | Parts by weight |
| --- | --- |
| Hydroxycitronellal | 100 |
| Linalool | 80 |
| Musk ketone | 80 |
| Phenylethyl alcohol | 60 |
| γ-Methyl ionone | 90 |
| Benzyl acetate | 70 |
| Undecyl aldehyde (10%) | 50 |
| Cyclamen aldehyde (10%) | 50 |
| Rhodinol | 40 |
| Heliotropin | 40 |
| α-Amylcinnamaldehyde | 30 |
| Natural civet | 30 |
| Vetiver oil | 30 |
| Coumarin | 20 |
| Rose absolute | 30 |
| Jasmine absolute | 30 |
| Bergamot oil | 30 |
| Ylang-ylang oil | 20 |
| Compound obtained in Example 1 | 120 |

This perfume composition emitted a harmonized fragrance having the scent of sandalwood. Similar results were obtained by repeating the same procedure except that, in the above formulation, the compound obtained in Example 2 was used in place of the compound obtained in Example 1. However, the fragrance of the latter perfume composition was lighter than that of the former perfume composition.

EXAMPLE 6

Using the tricyclo[2.2.1.0$^{2,6}$]heptane derivative mixture obtained in Example 3, a perfume base composition for use in toilet soaps was prepared according to the following formulation.

| Ingredient | Parts by weight |
| --- | --- |
| γ-Methyl ionone | 200 |
| Bergamot oil | 100 |
| Lemon oil | 30 |
| Ylang-ylang oil | 30 |
| Linalool | 50 |
| Linalyl acetate | 30 |
| Rhodinol | 15 |
| Rose absolute | 15 |
| Jasmine absolute | 15 |
| Orris concrete | 15 |
| Eugenol | 50 |
| Patchouli oil | 10 |
| Vetiver oil | 30 |
| Oakmoss absolute | 5 |
| Styrax oil | 20 |
| Rose oil | 5 |
| Cananga oil | 25 |
| Siam benzoin | 30 |
| Vanilla resin | 30 |
| Coumarin | 20 |
| Heliotropin | 40 |
| Petigrain oil | 50 |
| Musk ketone | 10 |
| Musk ambrette | 10 |
| Tolu balsam | 5 |
| Olibanum resin | 5 |
| Compound obtained in Example 3 | 150 |
| Guaiac wood oil | 5 |

When this perfume composition was blended with materials for the manufacture of soap, there was obtained soap emitting a pleasant odor having an oriental and sandalwood-like fragrance.

What is claimed is:

1. A tricyclo[2.2.1.0$^{2,6}$]heptane derivative of the general formula

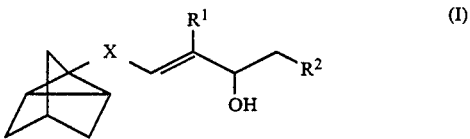

where X represents —CH$_2$CH$_2$— or

and R$^1$ and R$^2$ independently represent hydrogen or methyl.

2. A process for preparing a tricyclo[2.2.1.0$^{2,6}$]heptane derivative of the general formula

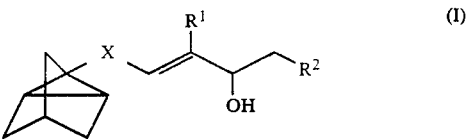

where X represents —CH$_2$CH$_2$— or

and R$^1$ and R$^2$ independently represent hydrogen or methyl, which comprises (a) reacting an aldehyde compound of the general formula

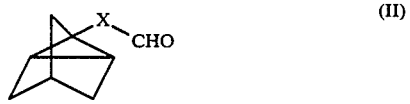

where X has the same meaning as described for formula (I), with a dialkyl ketone of the general formula $$R^1CH_2\overset{\overset{O}{\|}}{C}CH_2R^2$$

where $R^1$ and $R^2$ have the same meanings as described for formula (I), in the presence of an aldol condensation catalyst to obtain an α,β-unsaturated ketone of the general formula

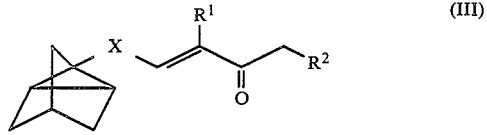

where X, $R^1$ and $R^2$ have the same meanings as described for formula (I), and then (b) reducing the resulting α,β-unsaturated ketone.

3. The process of claim 2 wherein the dialkyl ketone is 3-pentanone.

4. The process of claim 2 wherein the aldol condensation catalyst is a compound selected from the group consisting of alkali metal hydroxides, alkali metal alkoxides, quaternary ammonium hydroxides and alkali metal amides.

5. The process of claim 2 wherein the reduction is carried out with the aid of a metal hydride.

6. The process of claim 2 wherein the reduction is carried out according to the Meerwein-Ponndorf reduction.

7. A perfume composition containing a tricyclo[2.2.1.0$^{2,6}$]heptane derivative of the general formula

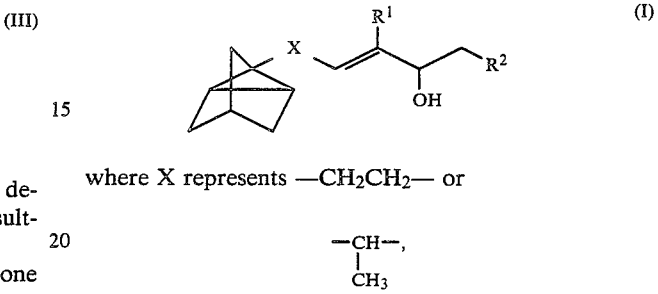

where X represents —CH$_2$CH$_2$— or $$-\underset{\underset{CH_3}{|}}{CH}-,$$

and $R^1$ and $R^2$ independently represent hydrogen or methyl.

* * * * *